United States Patent [19]
Wijesekera et al.

[11] Patent Number: 5,571,908
[45] Date of Patent: Nov. 5, 1996

[54] PORPHYRINS

[75] Inventors: Tilak Wijesekera, Glen Mills; James E. Lyons, Wallingford; Paul E. Ellis, Jr., Downingtown, all of Pa.

[73] Assignee: Sun Company, Inc. (R&M), Philadelphia, Pa.

[21] Appl. No.: 174,732

[22] Filed: Dec. 29, 1993

Related U.S. Application Data

[63] Continuation-in-part of Ser. No. 568,116, Aug. 16, 1990, which is a continuation-in-part of Ser. No. 425,089, Oct. 23, 1989, abandoned, which is a continuation-in-part of Ser. No. 66,666, Jun. 26, 1987, Pat. No. 4,900,871, which is a continuation-in-part of Ser. No. 246, Jan. 2, 1987, Pat. No. 4,895,682.

[51] Int. Cl.$^6$ .................................................. C07D 487/22
[52] U.S. Cl. ............................................................ 540/145
[58] Field of Search ............................................ 540/145

[56] References Cited

U.S. PATENT DOCUMENTS

| | | | |
|---|---|---|---|
| 4,803,187 | 2/1989 | Lyons et al. | 502/200 |
| 4,859,798 | 8/1989 | Lyons et al. | 568/399 |
| 4,892,941 | 1/1990 | Dolphin et al. | 540/145 |
| 4,895,680 | 1/1990 | Ellis, Jr. et al. | 260/413 |
| 4,895,682 | 1/1990 | Ellis, Jr. et al. | 260/413 |
| 4,900,871 | 2/1990 | Ellis, Jr. et al. | 568/399 |
| 4,970,348 | 11/1990 | Ellis, Jr. et al. | 568/399 |
| 5,091,354 | 2/1992 | Ellis, Jr. et al. | 502/200 |
| 5,120,882 | 6/1992 | Ellis, Jr. et al. | 568/910 |
| 5,120,886 | 6/1992 | Lyons et al. | 568/807 |
| 5,212,300 | 5/1993 | Ellis, Jr. et al. | 540/145 |
| 5,241,062 | 8/1993 | Wijesekera et al. | 540/145 |
| 5,252,698 | 10/1993 | Bhardwaj et al. | 528/230 |
| 5,280,115 | 1/1994 | Ellis, Jr. et al. | 540/145 |

OTHER PUBLICATIONS

Ellis, Jr. et al, Chemical Abstract 117:926266 (1992) for 471,561 (Feb. 19, 1992).
Lyons et al., "Selective Low Temperature Hydroxylation of Isobutane By Molecular Oxygen Catalyzed By An Iron Perhaloporphyrin Complex", *Cat. Lett.*, 8, 45 (1991).
Badger et al., "Porphyrins VII. The Synthesis of Porphyrins By the Rothemund Reaction", *Aust. J. Chem.*, 17, 1028–1035 (1964).
Osuka et al., "An Improved Synthesis of 5,15-Diaryloctaalkylporphyrins" *J. Heterocyclic Chem.*, 27, 1657 (1990).
Manka et al., "High Yield Synthesis of 5,15-Diarylporphyrins", *Tetrahedron Lett.*, 30, 6989 (1989).
Homma et al., "Electron Deficient Porphyrins, 1. Tetrakis (Trifluoromethyl) Porphyrin and Its Metal Complexes.", *Tetrahedron Lett.*, 24, 4343 (1983).
Ono et al., "A Convenient Synthesis of Trifluoromethylated Pyrroles and Porphyrins", *Bull. Chem. So. Jpn.*, 62, 3368 (1989).
Hoffmann et al., "Preparation and catalytic activities of the manganese and iron derivatives of $Br_8TMP$ and $Cl_{12}TMP$, two robust porphyrin ligands obtained by halogenation of tetramesitylporphyrin", *Bull. Soc. Chim. Fr.*, 129, 85 (1992).
Bhyrappa et al., "Octabromotetraphenylporphyrin and Its Metal Derivatives: Electronic Structure and Electrochemical Properties", *Inorg. Chem.*, 30, 239 (1991).
Onaka et al., "Porphyrin Synthesis in Clay Nanospaces", *Chemistry Lett.*, p. 117 (1993).
Gong et al., "Nitrooctaethylporphyrins: Synthesis, Optical and Redox Properties", *Can. J. Chem.*, 63, 401–405 (1985).
Ellis et al., "Halogen Substituent Effects on the Catalytic Activity of Iron Porphyrin Complexes for Selective Air-Oxidation of Alkanes in the Liquid Phase", *Cat. Lett.*, 3, 389, (1989).
Lyons et al., "Halogen Substituent Effects on the Catalytic Activity of Iron Porphyrin complexes for the Decomposition of tert-Butyl Hydroperoxide", *J. Catalysis*, 141, 311 (1993).
Lindsey et al., "Investigation of the Synthesis of Ortho–Substituted Tetraphenylporphyrins", *J. Org. Chem.*, 54, 828 (1989).
Adler et al., "On the Preparation of Metalloporphyrins", *J. Inorg. Nucl. Chem.*, 32, 2443 (1970).
J. B. Paine, III, in *The Porphyrins*, Dolphin ed., Academic Press, NY, v. 1, pp. 101, 163–234 (1978).
Ogoshi et al., "Syntheses of 5–Aryl– and 5,15–diaryl-2,3,7,8,12,13,17,18–Octaethylporphines" *Chem.Lett.*, p. 29, (1978).
Gunter et al., "Synthesis and Atropisomer Separation of Porphyrins Containing Functionalization at the 5,15–Meso Positions: Application to the Synthesis of Binuclear Ligand Systems" *J. Org. Chem.*, 46, 4792 (1981).
Young, et al., "Synthesis and Characterization of Blocked and Ligand–Appended Hemes Derived from Atropisomeric meso–Diphenylporphyrins", *J. Am. Chem. Soc.*, 107, 898 (1985).

*Primary Examiner*—Philip I. Datlow
*Attorney, Agent, or Firm*—Q. Todd Dickinson; Stephen T. Falk

[57] ABSTRACT

The invention comprises new compositions of matter, which are iron, manganese, cobalt or ruthenium complexes of porphyrins having hydrogen, haloalkyl or haloaryl groups in meso positions, two of the opposed meso atoms or groups being hydrogen or haloaryl, and two of the opposed meso atoms or groups being hydrogen or haloalkyl, but not all four of the meso atoms or groups being hydrogen. The invention also comprises new compositions of matter in which all four of the meso positions are substituted with haloalkyl groups and the beta positions are substituted with halogen atoms. A new method of synthesizing porphyrinogens is also provided.

The novel compositions and others made according to the process of the invention are useful as hydrocarbon conversion catalysts; for example, for the oxidation of alkanes and the decomposition of hydroperoxides.

13 Claims, No Drawings

PORPHYRINS

The government of the United States of America has rights in this invention pursuant to Cooperative Agreement No. DE-FC21-90MC26029 awarded by the U.S. Department of Energy.

This application is a continuation in part of pending application Ser. No. 07/568,116 filed Aug. 16, 1990, which was a continuation in part of application Ser. No. 07/425,089, filed Oct. 23, 1989, and now abandoned, which was a continuation in part of application Ser. No. 07/066,666, filed Jun. 26, 1987, now U.S. Pat. No. 4,900,871, which was a continuation in part of application Ser. No. 07/000,246, filed Jan. 2, 1987, now U.S. Pat. No. 4,895,682.

BACKGROUND OF THE INVENTION AND PRIOR ART

Electron deficient metalloporphyrins 1 (e.g. $R=C_6F_5$, X=F,Cl,Br,M=Fe) have been shown to be efficient catalysts for the highly selective air oxidation of light alkanes to alcohols (Ellis and Lyons, *Cat. Lett.*, 3, 389, 1989; Lyons and Ellis, *Cat, Let* 8, 45, 1991; U. S. Pat. Nos. 4,900,871; 4,970,348), as well as for efficient decomposition of alkyl hydroperoxides (Lyons and Ellis, *J. Catalysis*, 141, 311, 1993; Lyons and Ellis, U.S. Pat. No. 5,120,886).

They are prepared by co-condensation of pyrrole with the appropriate aldehyde (Badger, Jones and Leslett, "Porphyrins VII. The Synthesis of Porphyrins By the Rothemund Reaction", *Aust.J.Chem.*, 17, 1028–35, 1964; Lindsey and Wagner, "Investigation of the Synthesis of Ortho-Substituted Tetraphenylporphyrins", *J. Org. Chem.*, 54,828, 1989; U.S. Pat. Nos. 4,970,348; 5,120,882) followed by metal insertion (Adler, Longo, Kampas and Kim, "On the preparation of metalloporphyrins", *J. Inorg.Nucl.Chem.*, 32, 2443, 1970) and β-halogenation; (U.S. Pat. Nos. 4,8.92,941; 4,970,348). Ellis and Lyons U.S. Pat. No. 4,970,348 discloses chromium complexes of meso-tetrakis(trifluoromethyl)beta-haloporphyrins, made by reacting pyrrole with trifluoroacetaldehyde, and halogenating the resulting porphyrin; also, azide and hydroxide complexes of the porphyrins. Ellis and Lyons U.S. Pat. No. 5,120,882 discloses iron and other metal complexes of meso-tetrakis(trifluoromethyl)-beta-nitro-porphyrins, obtained by nitration of meso-tetrakis(trifluoromethyl)porphyrin.

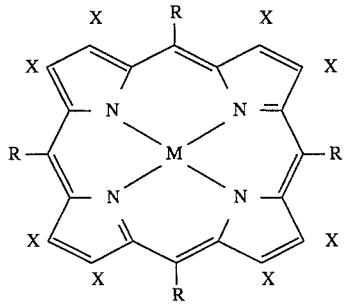

Dipyrromethanes (2; see J. D. Paine in *"The Porphyrins"* D. Dolphin, Ed., Academic Press, New York, Vol. I, pages 101 and 163–234, 1978) are the most commonly used precursors to a wide variety of symmetrical and unsymmetrical porphyrins. The use of dipyrromethanes for the synthesis of porphyrins carrying electron-withdrawing groups in all peripheral positions has been limited by the inaccessibility of 5,5'-unsubstituted dipyrromethanes in which the groups (2; $R^2,R^3,R^5,R^6$) that become the beta positions, and the group (2;$R^4$) that becomes the meso positions, of the resulting porphyrins, either electron-withdrawing or hydrogen for appropriate post-cyclization functionalization.

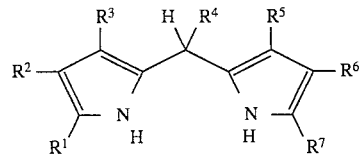

Acid-catalyzed co-condensation of 5,5-unsubstituted dipyrromethanes 3 with aldehydes 4 has been shown to give porphyrins (5; M=2H) in high yield. However, since the precursor dipyrromethanes 3 used in these disclosures are beta alkyl meso-unsubstituted systems ($R^1=R^2=R^4=R^5=$alkyl; $R^3=$H) and the aldehydes are aromatic aldehydes ($R^6=$aryl), the resulting porphyrins 5 are 5,15-diaryl-10,20 unsubstituted porphyrins with alkyl substitution at the beta positions ($R^1=R^2=R^4=R^5=$alkyl) (Ogoshi, Sugimoto, Nishiguchi, Watanabe, Matsuda and Yoshida, "Syntheses of 5-Aryl and 5,15-diaryl-2,3,7,8,12,13,17,18 Octaethylporphines" *Chemistry Lett.*, p.29, 1978; Gunter and Mander, "Synthesis and Atropisomer Separation of Porphyrins Containing Functionalization at the 5,15-Meso Positions: Application to the Synthesis of Binuclear Ligand Systems", *J. Org. Chem.*, 46, 4792, 1981; Young and Chang, "Synthesis and Characterization of Blocked and Ligand-Appended Hemes Derived from Atropisomeric meso Diphenylporphyrins", *J. Am. Chem. Soc.*" 107,898, 1985; Osuka, Nagata, Kobayashi and Maruyama, "An Improved Synthesis of 5,15-Diaryloctaalkylporphyrins', *J. Heterocyclic Chem.*, 27, 1657, 1990).

The fully unsubstituted dipyrromethane 3 ($R^1=R^2=R^3=R^4=R^5=$H) has also been condensed with substituted aromatic aldehydes 4 to give beta-unsubstituted 5,15-diarylporphyrins which are also unsubstituted at the other two meso positions 10 and 20 (5 $R^1=R^2=R^3=R^4=R^5=$H; $R^6=$aryl); Manka and Lawrence, "High Yield Synthesis of 5,15-Diarylporphyrins", *Tetrahedron Lett.*, 30, 6989, 1989).

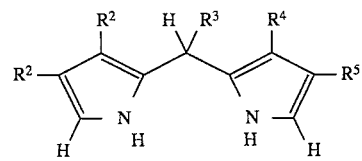

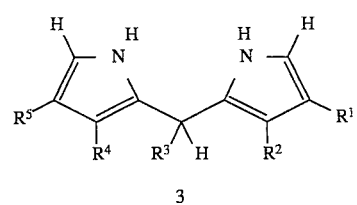

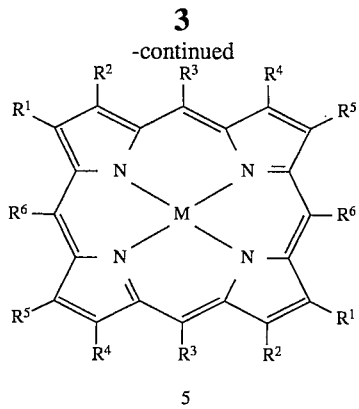

5

M. Homma et al, *Tetrahedron Lett.* 24, 4343 (1983) disclose Cu, Zn and Co complexes of porphyrins containing trifluoromethyl groups in β (beta) positions, such as 1,3,5, 7-tetrakis(trifluoromethyl)-2,4,6,8-tetraethylporphyrin.

N. Ono et al, *Bull.Chem.So.Jpn.* 62, 3368 (1989) also disclose zinc complexes of porphyrins containing trifluoromethyl groups in β positions, for example 1,3,5,7-tetrakis(trifluoromethyl)-2,4,6,8-tetramethylporphyrin.

Hoffman, Robert and Meunier, "Preparation and catalytic activities of the manganese and iron derivatives of $Br_8TMP$ and $Cl_{12}TMP$, two robust porphyrin ligands obtained by halogenation of tetramesitylporphyrin', *Bull.Soc.Chim.Fr.*, 129, 85, 1992, disclose ionic halogenation of tetramesitylporphyrin by N-bromosuccinimide or N-chlorosuccinimide to give as main product, meso-tetramesityl β-octabromoporphyrin and meso-tetrakis(3-chloro-2,4,6-trimethylphenyl-β-octachloroporphyrin, respectively, and that manganese and iron derivatives of these porhyrins are efficient catalysts for olefin epoxidation and alkane hydroxylation.

Lyons and Ellis, "Selective Low Temperature Hydroxylation of Butane By Molecular Oxygen Catalyzed By an Iron Perhaloporphyrin Complex", *Catalysis Lett.*, 8, 45, 1991 disclose synthesis of iron tetrakis(pentafluorophenyl) β-octabromoporphyrinato complexes, having unprecedented catalytic activity for the reaction of molecular oxygen with isobutane to give tert-butyl alcohol.

Bhyrappa and Krishnan, "Octabromotetraphenylporphyrin and Its Metal Derivatives: Electronic Structure and Electrochemical Properties", *Inorg.Chem.*, 30, 239, 1991 disclose $V^{IV}O$, Co(II), Ni(II), Cu(II), Zn(II), Pd(II), Ag(II) and Pt(II) derivatives of octabromotetraphenylporphyrin, and their electronic structure and electrochemical properties.

Onaka, Shinoda, Izumi and Nolen, "Porphyrin Synthesis in Clay Nanospaces", *Chemistry Lett.*, 117, 1993 disclose synthesis of meso-tetraalkylporphyrins from aliphatic aldehydes and pyrroles by using the clay, montmorillonite.

Gong and Dolphin, "Nitrooctaethylporphyrins: synthesis, optical and redox properties", *Can.,J.Chem*, vol. 63, 1985, pages 401–5, disclose reaction of zinc octaethylporphyrin with $N_2O_4$ in dichloromethane to give, in a stepwise reaction, the zinc complexes of mono-, di-, tri- and tetranitrooctaethylporphyrins, and demetallation of the products under acidic conditions to give the corresponding free base. The meso-nitro groups exert steric and electronic effects on the porphyrin macrocycle. N-protonation of the nitrated species causes a distortion of the ring and gives an optical spectrum similar to that of protonated meso-aryl substituted porphyrins. The nitro groups make the oxidation of the porphyrin ring more difficult and facilitate the ring reductions.

DESCRIPTION OF THE INVENTION

The present invention provides access for the first time to novel catalytically active metalloporphyrins carrying perhalocarbyl groups at two opposite meso positions (e.g.5,15) and which may also have other electron-withdrawing groups (perhalocarbyl, nitro) at the other two meso (10,20) positions. The novel catalysts of the invention are highly active for both alkane hydroxylation and hydroperoxide decomposition. The invention enables the synthesis of a series of catalytically active, highly electron deficient 5,15-(bis)halocarbyl metalloporphyrins with the 10,20 meso positions unsubstituted or carrying electron-withdrawing groups.

Since the syntheses provided by the invention may use meso-substituted-beta-unsubstituted dipyrromethanes (e.g. 3; $R^1=R^2=R^4=R^5=H;R^3=$halocarbyl), porphyrins 5 produced by co-condensation with appropriate aldehydes will in one embodiment of the invention carry electron-withdrawing groups in all four meso positions, while the beta positions will still be available for substitution by other electron-withdrawing groups. By using $R^6=H$ (HCHO or synthetic equivalent), 10,20-diunsubstituted porphyrins (5; $R^1=R^2=R_4=R^5=R^6=H$; $R^3=$halocarbyl) are synthesized, which can be substituted by electron-withdrawing groups (e.g. halogen, nitro). Any unsubstituted beta position on the porphyrin macrocycle can then be halogenated or nitrated according to known methods.

The invention comprises the following embodiments:

Method for synthesizing porphyrins by condensing a 5,5'-unsubstituted dipyrromethane (3; $R^3$ is H or halocarbyl) with formaldehyde or its equivalent or with a halocarbyl aldehyde (4; $R^6$ is H or halocarbyl). The product obtained where $3:R^3$ and $4:R^6$ are both hydrogen is a meso-unsubstituted porphyrinogen, which is subsequently converted to a meso-unsubstituted porphyrin. Where $3:R^3$ and $4:R^6$ are hydrogen and halocarbyl respectively, and when $3:R^3$ and $4:R^6$ are halocarbyl and hydrogen respectively, the product is a meso-halocarbylporhyrinogen having halocarbyl groups at two opposite meso positions (e.g.5,15) and hydrogen at the other two meso (10,20) positions. Where $3:R^3$ and $4:R^6$ are both halocarbyl, the product is a meso-tetrakis(halocarbyl)porphyrinogen. Where the product, after conversion of the porphyrinogen is porphine or meso-bis-hydrocarbylporphyrin, the meso hydrogens may be subsequently substituted with electron-withdrawing groups such as halogen, nitro or cyano substituents.

New compositions of matter comprising catalytically active iron, manganese, cobalt or ruthenium complexes of porphyrins having hydrogen or haloaryl at two opposite meso positions (5; $R^3$) and hydrogen or haloalkyl at the other two opposite meso positions (5; $R^6$) having hydrogen, halogen, nitro, cyano or halocarbyl at beta positions; and azide derivatives, oxo-bridged dimer derivatives of such complexes.

"Halocarbyl' as the term is used herein includes halohydrocarbyl and perhalocarbyl. "Perhalocarbyl" as used herein refers to complete substitution of halogen for hydrogen, or as near complete substitution as reasonably possible to attain under the circumstances.

Methods of Synthesizing Porphines

The invention in one embodiment provides novel methods for synthesizing porphyrins in which a dipyrromethane having formula 3 where $R^3$ is hydrogen or halocarbyl, preferably perhalocarbyl, for example trifluoromethyl, heptafluoropropyl, and $R^1$, $R^2$, $R^4$, and $R^5$ are independently hydrogen, alkyl, halogen, nitro, cyano or halocarbyl, is reacted with an aldehyde, $R^6CHO$, where $R^6$ is hydrogen or halocarbyl, preferably perhalocarbyl, for example pentafluorophenyl or trifluoromethyl, under co-condensation conditions to produce an intermediate porhyrinogen, and said intermediate porphyrinogen is converted to a meso-unsubstituted porphyrin (5; $R^3=R^6=H$) or to a porphyrin having halocarbyl groups in all four meso positions (5; $R^3$=halocarbyl, $R^6$=halocarbyl).

Where the beta positions of the porphyrin are unsubstituted in the above synthesis, that is, where $R^1$, $R^2$ $R^4$ and $R^5$ are hydrogen, the beta hydrogen atoms are available for substitution by electron-withdrawing atoms or groups such as halogen, nitro or cyano.

In another embodiment, in which the porphyrin produced has two halocarbyl groups in meso positions, and the other two meso positions (10,20) are unsubstituted, prepared by using in the condensation a halocarbyldipyrrcmethane (3; $R^3$=halocarbyl, for example trifluoromethyl, heptafluoropropyl)) and an aldehyde 4 in which $R^6$=H (HCHO or synthetic equivalent), porphyrins (5; $R^1=R^2=R^4=R^5=R^6=H$; $R^3$=halocarbyl) are obtained, which can be subsequently substituted in the two free meso positions by electron-withdrawing atoms and groups (5; $R^6$ is halogen, NO2, CN.

In the method according to this embodiment of the invention, the dipyrromethane and aldehyde are contacted with an acid catalyst, for example trifluoroacetic acid, hydrobromic acid or an insoluble acid such as clay, for example montmorillonite K-10, under co-condensation conditions. Conditions are used in the co-condensation which are within the knowledge of the person skilled in the art of co-condensation of dipyrromethanes and aldehydes.

Iron, manganese, cobalt and ruthenium, and particularly iron complexes of the porphyrins produced by the method of the invention are highly active catalysts for the hydroxylation of alkanes. Chromium complexes of the porphyrins produced by the method of this invention are disclosed in Ellis et al U.S. Pat. 4,970,348 above as catalysts for the oxidation of butane to methylethylketone; secondary butyl alcohol is disclosed as a minor product of the oxidation. For partial oxidation of alkanes to alcohols, the iron, cobalt, manganese and ruthenium complexes according to the invention are superior to the chromium complexes of said patent.

New Compositions of Matter

The invention also comprises embodiments wherein new compositions of matter having the structural formula 5 above, where $R^6$ is hydrogen or haloaryl, $R^3$ is hydrogen or haloalkyl, and $R^1$, $R^2$, $R^4$ and $R^5$ are independently hydrogen, halogen, nitro, cyano or halocarbyl, and M comprises iron, manganese, cobalt or ruthenium.

The invention also comprises new compositions of matter having the formula 5 where $R^3$ and $R^6$ are halocarbyl, $R^1$, $R^2$, $R^4$ and $R^5$ are halogen and M comprises iron, manganese, cobalt or ruthenium. These are metal complexes of perhalogenated meso tetraalkylporphyrins.

The new compositions of matter according to the invention include:
(1) the Fe, Mn, Co and Ru complexes of meso-bis(haloaryl)-bis(haloalkyl)porphyrins (5; M is M' or M'X, where M'=Fe, Mn, Co or Ru and X=halogen or hydroxyl, $R^1$, $R^2$, $R^4$ and $R^5$ are independently hydrogen, halogen, nitro, cyano or halocarbyl, $R^6$ is haloaryl and $R^3$ is haloalkyl);
(2) the Fe, Mn, Co and Ru complexes of meso-tetrahalocarbyl-beta-perhaloporphyrins 5; M is as in (1) above, $R^3$ and $R^6$ are halocarbyl and $R^1$, $R^2$, $R^4$ and $R^5$ are halogen);
(3) azide derivatives of substituted porphyrin metal complexes ($MPN_3$, where MP is a metal complex of a substituted porphyrin as disclosed in (1));
(4) oxo-bridged dimers of substituted porphyrin metal complexes as herein disclosed (MPOPM, where MP and PM are metal complexes of substituted porphyrins as disclosed in (1)).

Examples of the above categories include the porphyrins synthesized in Examples 2, 3, 4, 5, 8, 16 and 17 below, namely:

5,15-bis(pentafluorophenyl)-10,20-bis-(trifluoromethyl)-porphyrin (Example 2), the iron(III)chloride complex (Example 3) of the porphyrin of Example 2, the oxo-bridged dimer (Example 4) of the complex of Example 3, the azide derivative (Example 5) of the complex of Example 3, di(trifluoromethyl)porphyrin (Example 8), bis(pentafluorophenyl)-10,20-(trifluoromethyl)-β-octabromoporphyrinatoiron(III) (Example 16)

5, 10,15,20-tetrakis(trifluoromethyl)porphyrinatoiron(III) chloride (Example 17)

Following the co-condensation of dipyrromethane with aldehyde according to the invention, transition metal such as iron may be inserted into the porphyrins to prepare the catalytic species in their hemin, azide or oxo-bridged dimer forms. Where feasible, the hydroxide forms are also within the scope of the invention. Further modification of the porphyrins by substitution at the beta and meso positions with other electron-withdrawing groups (halogens, nitro, etc.) may be done before or after insertion of iron or other transition metal. The products have highly efficient catalytic behavior in both alkane hydroxylations and hydroperoxide decompositions.

Oxidation and Hydroperoxide Decomposition Methods

The invention is particularly useful for partially oxidizing alkanes to alcohols by contacting the alkane feedstock with oxygen and a transition metal complex of a porphyrin produced by the method of the invention. The feedstocks and operating conditions used in such operations are generally those described in U.S. Pat. Nos. 4,803,187; 4,859,798; 4,895,680; 4,895,682; 4,900,871; 4,970,348 and 5,091,354, the disclosures of which are hereby incorporated by reference.

The invention also provides a novel method for decomposing hydroperoxides to alcohols by contacting the hydroperoxide feedstock with oxygen and such transition metal complex. The feedstocks and process conditions used in such operation according to the invention are generally as set forth in Lyons and Ellis U.S. Pat. No. 5,120,886, the disclosure of which is hereby incorporated by reference.

The following examples illustrate the invention:

EXAMPLE 1

Synthesis of bis(pyrrol-2-yl)trifluoromethylmethane from pyrrole and trifluoroacetaldehyde methyl hemiacetal Pyrrole (150 mmol) and trifluoroacetaldehyde methyl hemiacetal (75 mmol) in tetrahydrofuran are heated at reflux with catalytic amounts of hydrochloric acid for 2 hours under an inert atmosphere. GC analysis of the reaction mixture indicated the presence of the desired dipyrromethane in greater than 80% yield. Neutralization of the acid followed by work up and chromatography gave the pure bis(pyrrol-2-yl)-trifluoromethylmethane 3 ($R^3$=$CF_3$)). MS:m/z=214. This preparation has been disclosed in Wijesekera U.S. patent application Ser. No. 08/143,261 filed on Oct. 26, 1993.

EXAMPLE 2

Synthesis of 5,15-bis(pentafluorophenyl-10-20-bis-(trifluoromethyl)-porphyrin from bis(pyrrol-2-yl)trifluoromethylmenthane and pentafluorobenzaldehyde Bis(pyrrol-2-yl)-trifluoromethylmethane (3; $R^3$=$CF_3$; $R^1$=$R^2$=$R^4$=$R^5$=H; 1.07 g; 5 mmol) and pentafluorobenzaldehyde (4;$R^4$=perfluorophenyl; 982 mg; 5 mmol) and hydrobromic acid (32% in acetic acid; 1 mL) were stirred in degassed chloroform (1 L) for 20 h at room temperature in the dark under a closed argon atmosphere. The intermediate porphyrinogen was treated with 2,3-dichloro-5,6-dicyano-1,4-benzoquinone (DDQ) and stirred for 3 h exposed to light and air. The crude reaction mixture was evaporated to dryness, the residue redissolved in chloroform and filtered through neutral alumina which retains excess oxidant and most of the byproducts. The pure product, 5,15-bis(pentafluorophenyl)-10,20-bis(trifluoromethyl)porphyrin, or $(C_6F_5)_2(CF_3)_2PH_2$ where P designates the porphryinato ligand ($5a$;$R^1$=$R^2$=$R^4$=$R^5$=H, $R^3$=$CF_3$, $R^6$=$C_6F_5$, M=2H), was obtained by evaporation of the filtrate to dryness and recrystallization of the residue from dichloromethane/methanol. MS:m/z=778; uv: λ max 408, 504, 538, 584, 638.

EXAMPLE 3

Preparation of the iron complex of 5,15-bis(pentafluorophenyl)-10,20-bis-(trifluoromethyl)porphyrin.

The porphyrin $5a$ prepared in Example 2 (200 mg), sodium acetate trihydrate (600 mg) and glacial acetic acid (90 mL) were degassed and heated with ferrous chloride (600 mg) for 20 min at 100° C. The reaction mixture was allowed to cool to room temperature and exposed to air overnight. Hydrochloric acid (3M;90 ML) was added to the reaction mixture and the precipitated solid was filtered and washed with water. The solid was redissolved in chloroform and chromatographed on neutral alumina. The iron complex was eluted using 2% $CH_3OH$-$CH_2Cl_2$. Treatment with hydrochloric acid (6M) produced the desired product, 5,15-bis(pentafluorophenyl)-10,20-bis(trifluoromethyl)porphyrinato iron(III)chloride, or $(C_6F_5)_2(CF_3)_2PFeCl$ ($5b$; $R^1$=$R^2$=$R^4$=$R^5$=H, $R^3$=$CF_3$, $R^6$=$C_6F_5$, M=FeCl. MS: m/z=867 (M+), 832 (M+-Cl); UV: λ max, 350/408 (split Soret), 508(wk), 622(wk) nm.

EXAMPLE 4

Preparation of oxo-bridged dimer of iron complex of 5,15-bis(penta-fluorophenyl-10,20-bis-(trifluoromethyl)porphyrin The iron complex $5b$ prepared in Example 3 (100 mg) dissolved in toluene (50 mL) was stirred with aqueous sodium hydroxide (2M;50 ml) for 30 min. The organic layer was separated, washed with water (2×40 mL), concentrated and passed through neutral alumina (Brockman activity V). The eluate was evaporated to dryness to give the oxo-bridged dimer $[(C_6F_5)_2(CF_3)_2PFe]_2O$ ($5c$; $R^1$=$R^2$=$R^4$=$R^5$=H, $R^3$=$CF_3$, $R^6$=$C_6F_5$, M=Fe-O-FeP) FABMS:m/z=1680 (M+), 832(M+-OFeP); UV: λ max, 332(wk), 388(Soret), 422(sh),562,602 nm.

EXAMPLE 5

Preparation of azide derivative of iron Complex of 5,15-bis(penta-fluorophenyl-10,20-bis-(trifluoromethyl)porphyrin The iron complex $5b$ prepared in Example 3 (43 mg) dissolved in dry acetone (6 mL) was stirred with sodium azide (45 mg) for 45 h. The solid was filtered and the filtrate was evaporated to dryness. The residue was redissolved in dry dichloromethane, filtered and the solvent removed to isolate the azide derivative $(C_6F_5)_2(CF_3)_2PFeN_3$ ($5d$; $R^1$=$R^2$=$R^4$=$R^5$=H, $R^3$=$CF_3$, $R^6$=$C_6F_5$, M=FeN$_3$) exhibiting a characteristic azide stretching frequency in the IR spectrum at 2042 cm−1.

EXAMPLE 6

Synthesis of 5,10,15,20-tetrakis(trifluoromethyl)porphyrin from bis-(pyrrol-2-yl)trifluoromethylmethane and trifluoroacetaldehyde methyl hemiacetal Equimolar quantities of bis(pyrrol-2-yl)-trifluoromethylmethane (3; $R^1$=$R^2$=$R^{4=R5}$=H, $R^3$=$CF_3$) and trifluoroacetaldehyde methyl hemiacetal (4; $R^6$=$CF_3$ as the hemiacetal) were heated at reflux for 8 h in degassed chloroform in the presence of catalytic amounts of trifluoroacetic acid. The solution was allowed to cool to room temperature and treated, dropwise with a solution of 2,3-dichloro-5,6-dicyano-4-benzoquinone (DDQ) in benzene over 15 min. The reaction mixture was reheated at reflux for 3 h, cooled to room temperature and the porphyrin $(CF_3)_4PH_2$ ($5e$; $R^1$=$R^2$=$R^4$=$R^5$=H, $R^3$=$R^6$=$CF_3$, M=2H) isolated by passing through neutral alumina. MS:m/z=582 (M+). UV: λ max, 404 (Soret), 510, 544, 594, 648 nm.

EXAMPLE 7

Preparation of the iron complex of 5,10,15,20-tetrakis(trifluoromethyl)-porphyrin The porphyrin $5e$ prepared in Example 6 (30 mg), sodium acetate trihydrate (100 mg) and acetic acid (12 mL) were degassed and heated with ferrous chloride (150 mg) for 20 min at 120° C. The reaction mixture was allowed to cool to room temperature and exposed to air overnight. Hydrochloric acid (3M) was added to the reaction mixture and the precipitated solid filtered and washed with 2M HCl. The solid was redissolved in chloroform, the solution extracted once with 6N HCl, the organic layer separated and evaporated to dryness. The product, 5,10,15,20-tetrakis(trifluoromethyl)porphyrinatoiron(III) chloride, or $(CF_3)_4PFeCl$ ($5f$; $R^1$=$R^2$=$R^4$=$R^5$=H, $R^{3=R6}$=$CF_3$, M=FeCl) was isolated by redissolving in dichloromethane and crystallizing from n-hexane. UV: 348/404 (split Soret), 506(wk), 640(wk) nm. MS: m/z, 671/673 (M+), 636 (M-Cl).

EXAMPLE 8

Synthesis of 5,15-bis(trifluoromethyl)porphyrin from bis(pyrrol-2-yl)trifluoromethylmethane and dimethoxymethane Equimolar quantities of bis(pyrrol-2-yl)-trifluoromethylmethane (3; $R^1=R^2=R^4=R^5=H$, $R^3=CF_3$) and dimethoxymethane (4; $R^6=H$ as the dimethyl acetal), were refluxed for 3 h in degassed chloroform with catalytic amounts of hydrobromic acid. The cooled reaction mixture was stirred with a solution of DDQ in benzene overnight, passed through neutral alumina (Brockman activity V) to isolate the porphyrin $(CF_3)_2PH_2$ (5 g; $R^1=R^2=R^4=R^5=R^6=H$, $R^3=CF_3$, M=2H— MS:m/z=446(M+), UV: λ max,396 (Soret), 498,534,576,626 nm.

EXAMPLE 9

Partial Oxidation of Isobutane with Oxo-Bridged Dimer of the Iron Complex of 5,15-bis(pentafluorophenyl-10,20-bis (trifluoromethyl)-porphyrin as the Catalyst The catalyst $[(C_6F_5)_2(CF_3)_2PFe]_2O$ prepared in Example 4 (5c;0.0065 mmol) was dissolved in benzene (25 mL) and isobutane (7 g) added. Oxygen (5 bars) was pressed on the stirred solution at 60° C. for six hours. After this time, the solution was cooled, brought to atmospheric pressure and analyzed by standardized glpc. It was determined that 530 moles of isobutane had reacted per gram-atom of iron used in the catalyst. The selectivity to tert-butyl alcohol was over 85% with acetone and di-tert-butylperoxide being minor products.

EXAMPLE 10

Repeat of Example 9 with Higher Reaction Temperature

A catalytic reaction was run under the conditions of Example 9 except that the reaction temperature was 80° C. Under these conditions, 1270 moles of isobutane reacted per gram-atom of iron used and tert-butyl alcohol was the predominant product.

EXAMPLE 11

Partial Oxidation of Isobutane with Azide Derivative of Iron Complex of 5,15-bis(pentafluorophenyl-10,20-bis- (triflucromethyl)porphyrin A catalytic reaction was run under the conditions of Example 10 except that the catalyst used was $(C_6F_5)_2(CF_3)_2PFeN_3$ (5d;0.013 mmole) prepared in Example 5. Over 1330 moles of isobutane reacted per gram-atom of iron used and tert-butyl alcohol was the predominant product.

EXAMPLE 12

Comparison Example using unhalogenated metalloporphyrin complexes

To illustrate the high activity of the above complexes relative to unhalogenated metalloporphyrin complexes, experiments were conducted under the conditions of Example 11 except that the catalyst was meso-tetraphenylporphyrinatoiron(III) chloride [Fe(TPP)Cl] or octaethylporphyrinatoiron(III) chloride [Fe(OEP)Cl] or octaethylporphyrinatoiron(III) azide [Fe(OEP)N_3], and no reaction occurred in any of the three cases.

EXAMPLE 13

Decomposition of Hydroperoxide Using the Catalyst of Example 3

The complex $(C_6F_5)_2(CF_3)_2PFeCl$ prepared in Example 3 (5b, 0.6 mg) was directly added to a stirring solution of tert-butylhydroperoxide (TBHP, 13.8 g) in tert-butyl alcohol (TBA, 18.1 g) at 80° C. Oxygen was rapidly evolved and the TBHP converted largely to TBA. Oxygen evolution was monitored manometrically with time. After a four hour reaction period, the reaction mixture was analyzed by standardized glpc. The TBHP conversion level was 97%. Product selectivities were: TBA (90%), acetone (5.1%) and di-tert-butylperoxide DTBP (2.4%).

EXAMPLE 14

Decomposition of Hydroperoxide Using Catalyst of Example 4

A reaction was run under conditions of Example 13 except that the catalyst used was $[(C_6F_5)_2(CF_3)_2PFe]_2O$ (5c) prepared in Example 4. After a 3.5 hour reaction period, the TBHP conversion level had reached 96% and the product selectivities were: TBA (88%), acetone (6.2%) and DTBP (2.6%).

EXAMPLE 15

Comparison Decomposition of Hydroperoxide Using Unhalogenated Complex as Catalyst To illustrate that the complexes of Examples 13 and 14 have exceptional activity, a reaction was run under conditions of Example 13, except that the catalyst was the unhalogenated complex, Fe(OEP)Cl. Very slow oxygen evolution was observed and after a 3.7 hour reaction period, the TDHP conversion level had reached only 11%. Furthermore, the catalyst had become completely inactive.

EXAMPLE 16

Synthesis of 5,15-bis(pentafluorophenyl)-10,20-bis (tribluoromethyl)-β-octabromoporphyrinatoiron(III) chloride 5,15-bis(pentafluorophenyl)-10,20-bis(trifluoromethyl)-porphyrinatoiron(III) chloride 5b, prepared in Example 3 (110 mg) is placed in dry carbon tetrachloride (40 mL) and pyridine (2 mL) and heated to reflux. A solution of bromine (0.5 mL) in carbon tetrachloride (2 mL) is added and continued heating at reflux for 10 h. The solution is allowed to cool to room temperature and the supernatant solution decanted. The residue is dissolved in 6M hydrochloric acid, washed with chloroform. The combined organic layers are extracted with 6M hydrochloric acid followed by 2M aqueous sodium hydroxide, washed with water and evaporated to dryness. The residue is dissolved in chloroform, the solution filtered through a pad of aluminal (neutral) and evaporated to dryness to give the title compound.

EXAMPLE 17

Synthesis of 5,10,15,20-tetrakis(trifluoromethyl)-β-octabromoporphyrinatoiron(III) chloride 5,1-0,15,20-tetrakis(trifluoromethyl)porphyrinatoiron(III) chloride 5f as prepared in Example 7, is β-brominated as described in Example 16 to give the analogous β-brominated derivative.

The invention claimed is:

1. Composition of matter having the following structural formula:

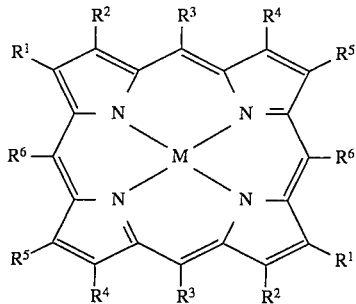

where M is a metal with or without halide, hydroxide or azide or with or without an oxo bridge form an oxo-bridged dimer, where said metal is iron, manganese, cobalt or ruthenium and (a) $R^6$ is hydrogen or haloaryl, $R^3$ is hydrogen or haloalkyl, but $R^6$ and $R^3$ are not both hydrogen, and where $R^1$, $R^2$, $R^4$ and $R^5$ are independently hydrogen, hydrocarbyl, halogen, nitro, cyano or halocarbyl, or (b) $R^3$ is haloalkyl and $R^6$ is haloalkyl but $R^3$ and $R^6$ are not the same haloalkyl, and $R^1$, $R^2$, $R^4$ and $R^5$ are halogen.

2. Composition of matter according to claim 1 wherein $R^6$ is hydrogen and $R^3$ is haloalkyl.

3. Composition of matter according to claim 2 wherein $R^3$ is perfluoroalkyl.

4. Composition of matter according to claim 1 wherein $R^6$ is haloaryl and $R^3$ is hydrogen.

5. Composition of matter according to claim 4 wherein $R^6$ is perfluoroaryl.

6. Composition of matter according to claim 1 wherein $R^6$ is pentafluorophenyl and $R^3$ is trifluoromethyl.

7. Composition of matter according to claim 1 wherein $R^3$ and $R^6$ are haloalkyl and $R^1$, $R^2$, $R^4$ and $R^5$ are halogen.

8. Composition of matter according to claim 7 wherein $R^3$ and $R^6$ are perfluoroalkyl and said halogen is bromine.

9. Composition of matter according to claim 7 wherein $R^3$ and $R^6$ are perfluoroalkyl and said halogen is chlorine.

10. Composition comprising an oxo-bridged dimer of claim 1.

11. Composition comprising an azide of claim 1.

12. Composition of matter according to claim 1 wherein M is iron.

13. Composition of matter according to claim 12 wherein said iron is present as iron(III)halide.

* * * * *